United States Patent
He et al.

(10) Patent No.: US 11,497,437 B2
(45) Date of Patent: Nov. 15, 2022

(54) SLEEP MONITORING CIRCUIT AND SLEEP MONITORING APPARATUS

(71) Applicant: SHENZHEN EEGSMART TECHNOLOGY CO., LTD., Shenzhen (CN)

(72) Inventors: Chao He, Shenzhen (CN); Yu Song, Shenzhen (CN); Wencai Du, Shenzhen (CN); Huawei Ma, Shenzhen (CN)

(73) Assignee: Shenzhen Eegsmart Technology Co., Ltd., Shenzhen (CN)

(*) Notice: Subject to any disclaimer, the term of this patent is extended or adjusted under 35 U.S.C. 154(b) by 390 days.

(21) Appl. No.: 16/643,547

(22) PCT Filed: Apr. 23, 2018

(86) PCT No.: PCT/CN2018/084104
§ 371 (c)(1),
(2) Date: Feb. 29, 2020

(87) PCT Pub. No.: WO2019/041841
PCT Pub. Date: Mar. 7, 2019

(65) Prior Publication Data
US 2020/0196941 A1    Jun. 25, 2020

(30) Foreign Application Priority Data
Sep. 1, 2017 (CN) .......................... 201710779570.9

(51) Int. Cl.
*A61B 5/00* (2006.01)
*A61B 5/024* (2006.01)
(Continued)

(52) U.S. Cl.
CPC .......... *A61B 5/4806* (2013.01); *A61B 5/6833* (2013.01); *H02J 7/007* (2013.01);
(Continued)

(58) Field of Classification Search
None
See application file for complete search history.

(56) References Cited

U.S. PATENT DOCUMENTS 10,971,938 B2 * 4/2021 Park .......................... H02J 7/00
10,973,424 B2 * 4/2021 Lee ....................... H04N 5/2258
(Continued)

FOREIGN PATENT DOCUMENTS

CN    102499672 A    6/2012
CN    104757948 A    7/2015
(Continued)

*Primary Examiner* — Curtis A Kuntz
*Assistant Examiner* — Jerold B Murphy
(74) *Attorney, Agent, or Firm* — Robert L. Stearns; Dickinson Wright, PLLC

(57) ABSTRACT

A sleep monitoring circuit and a sleep monitoring apparatus are provided, in the circuit: a bidirectional receiving unit includes an electrode pad, and when the electrode pad receives a power supply signal, a handover control unit generates a charging control signal according to the power supply signal, so as to control a charging unit to perform charging management; when the electrode pad receives a bioelectric signal, a command acquisition unit acquires from a user a sleep monitoring command, so as to trigger an enabling unit to generate a monitoring handover signal, the handover control unit outputs a bioelectric signal to a bioelectric signal pick-up unit according to the monitoring handover signal, causing the bioelectric signal pick-up unit to extract feature information from the bioelectric signal and output same to a sleep monitoring unit, and the sleep monitoring unit generates a person sleep monitoring result according to the feature information.

18 Claims, 2 Drawing Sheets

(51) Int. Cl.
    *A61B 5/291*     (2021.01)
    *H02J 7/00*     (2006.01)
    *A61B 5/145*     (2006.01)

(52) U.S. Cl.
    CPC ....... *A61B 5/02438* (2013.01); *A61B 5/14542* (2013.01); *A61B 5/291* (2021.01); *A61B 2562/0209* (2013.01)

(56) References Cited

U.S. PATENT DOCUMENTS

| | | | |
|---|---|---|---|
| 11,327,443 B1* | 5/2022 | Trapero Martin | A61B 5/7475 |
| 2014/0008984 A1* | 1/2014 | Kamiyama | H02J 9/06 |
| | | | 307/64 |
| 2016/0192856 A1* | 7/2016 | Lee | A61B 5/0006 |
| | | | 600/382 |

FOREIGN PATENT DOCUMENTS

| | | | | |
|---|---|---|---|---|
| CN | 205072837 U | | 3/2016 | |
| CN | 107550462 A | | 1/2018 | |
| GB | 2394294 A | * | 4/2004 | ........... A61B 5/0006 |
| GB | 2394294 A | | 4/2004 | |

* cited by examiner

SLEEP MONITORING CIRCUIT AND SLEEP MONITORING APPARATUS

CROSS REFERENCE TO RELATED APPLICATIONS

The present application is a 35 U.S.C. § 371 national stage application of PCT Application Ser. No. PCT/CN2018/084104 filed on Apr. 23, 2018, which claims priority to Chinese Patent Application Ser. No. CN201710779570.9 filed on Sep. 1, 2017, the entire contents of which are incorporated herein by reference in their entireties.

TECHNICAL FIELD

The present application relates to the technical field of sleep monitoring, and particularly to a sleep monitoring circuit and a sleep monitoring apparatus.

BACKGROUND

Sleep quality is one of the important factors affecting physical health, so more and more people are paying attention to their sleep quality, and thereby more and more sleep monitoring apparatuses have emerged on the market.

Sleep monitoring apparatuses are usually configured as products worn by the human body in order to more closely test bioelectric signals from the human body. Existing sleep monitoring apparatuses are generally provided with a traditional exposed charging plug (or charging interface) and a bioelectric signal acquisition terminal, so that charging is performed through the charging plug (or charging interface) when charging is required, and the bioelectric signals is acquired through the acquisition terminal when sleep monitoring is required. However, such a setting makes the sleep monitoring apparatus unable to be waterproof due to the open exposure of the charging plug or charging interface, therefore the apparatus is under a risk of potentially leaking electricity or being damaged, which reduces the life of the apparatus. Moreover, due to the existence of the charging plug, the sleep monitoring apparatus cannot meet the demand of convenient portability from the user, which reduces the user's product experience. There are also some existing sleep monitoring apparatuses that are charged through a form of wireless charging, but the arrangement of the wireless charging greatly increases the production cost of the sleep monitoring apparatuses.

Therefore, the existing sleep monitoring apparatus has the problems of no waterproof, poor convenience, short service life, and high production cost.

TECHNICAL PROBLEMS

The purpose of the present application is to provide a sleep monitoring circuit and a sleep monitoring apparatus, which aim to solve the problems existed in the existing sleep monitoring apparatus with no waterproof, poor convenience, short service life, and high production cost.

SUMMARY

A first aspect of the present application provides a sleep monitoring circuit, and the sleep monitoring circuit includes:

a bidirectional receiving unit including an electrode patch, wherein the electrode patch receives a power signal from a charging apparatus when connected with the charging apparatus and receives a bioelectric signal from a human body when connected with the human body;

a command acquisition unit configured to acquire a sleep monitoring command from a user;

an enabling unit configured to generate a monitoring switch signal according to the bioelectric signal and the sleep monitoring command, wherein an input end of the enabling unit is connected with the bidirectional receiving unit, and an enabling end of the enabling unit is connected with an output end of the command acquisition unit;

a switch control unit configured to realize switch between a sleep monitoring function and a charging function, generate a charging control signal according to the power signal, and output the bioelectric signal according to the monitoring switch signal, wherein an input end of the switch control unit is connected with a first output end of the bidirectional receiving unit, a first enabling end of the switch control unit, a second output end of the bidirectional receiving unit and the input end of the enabling unit are connected together, and a second enabling end of the switch control unit is connected with an output end of the enabling unit;

a charging unit configured to implement charging management according to the charging control signal, wherein an input end of the charging unit is connected with a first output end of the switch control unit;

a bioelectric signal pickup unit configured to perform extraction on the bioelectric signal output by the switch control unit and generate characteristic information of the bioelectric signal, wherein an input end of the bioelectric signal pickup unit is connected with a second output end of the switch control unit;

a sleep monitoring unit configured to monitor and analyze the characteristic information and generate a monitoring result for human sleep, wherein an input end of the sleep monitoring unit is connected with an output end of the bioelectric signal pickup unit.

A second aspect of the present application provides a sleep monitoring apparatus, and the sleep monitoring apparatus includes the sleep monitoring circuit described above, wherein the electrode patch is plugged into a base of the charging apparatus or fit on a skin surface of a human body.

BENEFICIAL EFFECTS

In the sleep monitoring circuit provided in the present application, when the electrode patch accesses the power signal during connection with the charging device, the switch control unit generates the charging control signal according to the power signal, and then the charging unit performs the charging management according to the charging control signal; when the electrode patch accesses the bioelectrical signal during access to the human body, the command acquisition unitacquires the sleep monitoring command from the user, the enabling unit generates the monitoring switch signal according to the bioelectrical signal and the sleep monitoring command, so that the switch control unit outputs the bioelectric signal according to the monitoring switch signal, the bioelectric signal pickup unit extracts the characteristic information from the bioelectric signal and outputs the characteristic information to the sleep monitoring unit, and the sleep monitoring unit monitor the characteristic information and generates the monitoring result for human sleep. This circuit has a simple structure, can realize the switch between the sleep monitoring function and the charging function, and is low-cost. Moreover, the design of this circuit module makes the monitoring apparatus more portable and more suitable for the user to wear; and makes the apparatus be provided with waterproof, improves the service life, and avoids occurrence of an electric leakage accident and an electric shock accident, thereby improving the user experience.

EMBODIMENTS OF THE PRESENT APPLICATION

In order to make the technical problems to be solved, the technical solutions and the beneficial effects of the present application more clear and comprehensible, the present application will be further described in detail below with reference to the accompanying drawings and embodiments. It should be understood that, the specific embodiments described herein are merely to illustrate the present application and are not intended to limit the present application.

In the description of the present application, it should be understood that the terms "first" and "second" are only used for descriptive purposes, and cannot be understood as indicating or suggesting relative importance or implicitly indicating the number of the indicated technical features. Therefore, the features defined with "first" and "second" may explicitly or implicitly include one or more of the features. In the description of the present application, the term "a plurality of" means two or more, unless it is explicitly and specifically defined otherwise.

Figure 1:
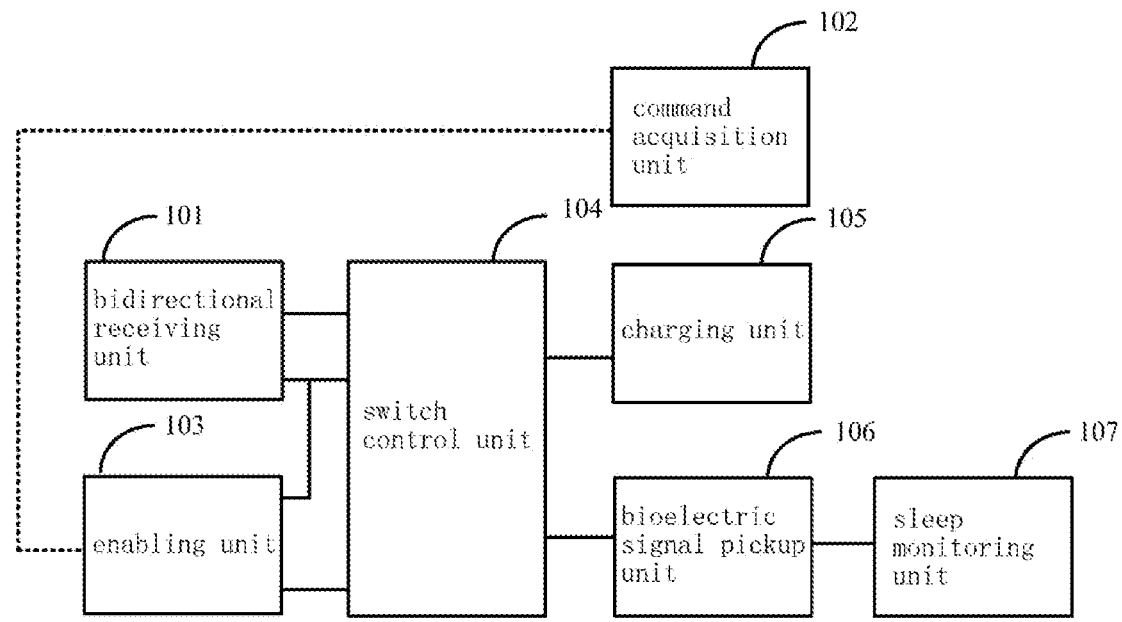
FIG. 1 is a structural schematic diagram of the sleep monitoring circuit according to an embodiment of the present application.

FIG. 1 shows a structural schematic diagram of the sleep monitoring circuit according to an embodiment of the present application. For convenience of illustration, only parts related to the present application are shown, which are detailed as follows.

A sleep monitoring circuit includes a bidirectional receiving unit 101, a command acquisition unit 102, an enabling unit 103, a switch control unit 104, a charging unit 105, a bioelectric signal pickup unit 106, and a sleep monitoring unit 107.

The bidirectional receiving unit 101 includes an electrode patch, which receives a power signal from a charging apparatus when connected with the charging apparatus and receives a bioelectric signal from a human body when connected with the human body.

In an embodiment of the present application, the bidirectional receiving unit 101 includes an electrode patch, and the electrode patch accesses a power signal by plugging into a base of the charging apparatus. Since many components of human skin tissue have certain electrical characteristics, the electrode patch may also be separated from the base of the charging apparatus and fit on the surface of the human skin (for example, closely fit on the forehead of the human body), and acquire the bioelectric signal through connecting to the human skin. Among them, the power signal accessed from the electrode patch is 4.5V-5.2V, while the voltage amplitude of the bioelectric signal from the human body is not more than 0.1V. For example, the voltage amplitude of the electroencephalogram(EEG) signal is the level of μV, which is generally in a range of several μV to dozens of μV. The electrode patch may be made of a conductive carbon film and a conductive mucous membrane, and the conductive carbon film is provided with an insulating layer, and the conductive mucous membrane is provided with a plastic protective layer, so that the electrode patch may access the power signal of the charging apparatus through plugging into the base of the charging apparatus and acquire the bioelectric signal through fitting on the surface of the human skin and at the same time have functions of effective waterproof and leakage proof while the electrode patch. The bidirectional receiving unit 101 outputs the charging voltage or bioelectric signal accessed by the electrode patch to the switch control unit 104, and a first output end and a second output end of the bidirectional receiving unit 101 are respectively connected with an input end and a first enabling end of the switch control unit 104.

The command acquisition unit 102 is configured to acquire a sleep monitoring command from a user.

The enabling unit 103 is configured to generate a monitoring switch signal according to the bioelectric signal and the sleep monitoring command. An input end of the enabling unit 103 is connected with the second output end of the bidirectional receiving unit 101, and an enabling end of the enabling unit 103 is connected with an output end of the command acquisition unit 102.

In an embodiment of the present application, the command acquisition unit 102 is configured to acquire the sleep monitoring command input by the user, and at the same time send the acquired sleep monitoring command to the enabling unit 103, so that the enabling unit 103 generates the monitoring switch signal according to the bioelectricity signal and the sleep monitoring command, and outputs the monitoring switch signal to the switch control unit 104. The switch signal is 2.7V-12V, and the output end of the command acquisition unit 102 is connected with the enabling end of the enabling unit 103. Specifically, the enabling unit 103 may be connected with the command acquisition unit 102 through a wireless network, so as to acquire the monitoring switch signal of the command acquisition unit 102 through radio wave. For example, the command acquisition unit 102 may be combined by hardware and software for command acquisition, and may specifically bean intelligent terminal of a sleep monitoring APP. The user inputs the sleep monitoring command to the command acquisition unit 102 by opening the sleep monitoring APP, and then the command acquisition unit 102 links to the enabling unit 103 through Bluetooth, thereby enabling the enabling unit 103 to generate the monitoring switch signal according to the sleep monitoring command and output the monitoring switch signal to the switch control unit 104.

The switch control unit 104 is configured to switch between the sleep monitoring function and the charging function, and to generate a charging control signal according to the power signal, and to output the bioelectric signal according to the monitoring switch signal. The input end of the switch control unit 104 is connected with the first output end of the bidirectional receiving unit 101, the first enabling end of the switch control unit 104, the second output end of the bidirectional receiving unit 101 and the input end of the enabling unit 103 are connected together, and the second enabling end of the switch control unit 104 is connected with the output end of the enabling unit 103.

In an embodiment of the present application, the switch control unit 104 is provided with two switch modes, and switches into a corresponding mode according to the accessed signal. Specifically, when the switch control unit 104 receives the power signal output by the bidirectional receiving unit 101, the voltage is enough to trigger the switch control unit 104 to switch into the first function mode (i.e. the charging function mode) because the power signal is 4.5V-5.2V, and the switch control unit 104 generates the charging control signal according to the power signal and outputs the charging control signal to the charging unit 105; when the switch control unit 104 receives the bioelectric signal input by the bidirectional receiving unit 101, the voltage amplitude is weak and the voltage is not enough to trigger the switch control unit 104 to switch into the first function mode because the bioelectric signal is not greater than 0.1V, at this time the enabling unit 103 will generate the monitoring switch signal according to the sleep monitoring command if the command acquisition unit 102 acquires the sleep monitoring command from the user. Since the monitoring switch signal is 2.7V-12V, the voltage is enough to trigger the switch control unit 104 to switch into the second function mode (i.e. the sleep monitoring function mode), and the switch control unit 104 outputs the acquired bioelectric signal to the bioelectric signal pickup unit 106 according to the monitoring switch signal.

The charging unit 105 is configured to implement charging management according to the charging control signal, and an input end of the charging unit 105 is connected with the first output end of the switch control unit 104. Specifically, the charging unit 105 implements the charging management according to the charging control signal, detects electric quantity of a battery, and determines whether to disconnect charging for the battery according to a measurement result.

In an embodiment of the present application, the charging unit 105 receives the charging control signal output by the switch control unit 104, implements the charging management according to the charging control signal, and charges the battery.

The bioelectric signal pickup unit 106 is configured to perform extraction on the bioelectric signal output by the switch control unit 104 and generate characteristic information of the bioelectric signal, and an input end of the bioelectric signal pickup unit 106 is connected with the second output end of the switch control unit 104.

In an embodiment of the present application, the bioelectric signal pickup unit 106 receives the bioelectric signal output by the switch control unit 104, extracts the characteristic information of the bioelectric signal according to the bioelectrical signal, and at the same time outputs the extracted characteristic information to the sleep monitoring unit 107 to realize monitoring of the human sleep condition. Specifically, the bioelectric signal pickup unit 106 performs a digital-to-analog conversion on the input bioelectrical signal, and extracts the characteristic information with a specific voltage waveform from the digital-to-analog converted signal. The characteristic information includes physiological data information when the user sleeps, such as an energy proportion of various wavebands of the user's EEG wave, or a fluctuation characteristic of heart rate values or the blood oxygen values. Therefore, a circuit is qualified as long as the circuit is capable of realizing the above functions of the bioelectric signal pickup unit 106, for example, a circuit including a biosensor, a digital-to-analog converter and signal extraction.

The sleep monitoring unit 107 is configured to monitor and analyze the characteristic information and generate a monitoring result for human sleep, and an input end of the sleep monitoring unit 107 is connected with the output end of the bioelectric signal pickup unit 106.

In an embodiment of the present application, the sleep monitoring unit 107 receives the characteristic information input by the bioelectric signal pickup unit 106, monitors and analyzes the characteristic information, and generates the monitoring result for the human sleep to obtain the user's sleep condition. For example, according to the energy proportion of the various wavebands of the user's EEG wave or the fluctuation characteristic of the heart rate values or the blood oxygen values etc. input by the bioelectric signal pickup unit 106, the user's sleep stage (for example, the awake stage, the shallow sleep stage, the deep sleep stage) and the sleep condition are monitored and analyzed. Therefore, a circuit is qualified as long as the circuit is capable of realizing the functions of the sleep monitoring unit 107.

In the sleep monitoring circuit provided in the present application, when the electrode patch accesses the power signal, the switch control unit 104 generates the charging control signal according to the power signal so as to control the charging unit 105 to perform the charging management; when the electrode patch accesses the bioelectrical signal, the command acquisition unit 102 acquires the sleep monitoring command from the user to trigger the enabling unit 103 to generate the monitoring switch signal, and the switch control unit 104 outputs the bioelectric signal to the bioelectric signal pickup unit 106 according to the monitoring switch signal, so that the bioelectric signal pickup unit 106 extracts the characteristic information from the bioelectric signal and outputs the characteristic information to the sleep monitoring unit 107, and the sleep monitoring unit 107 generates the monitoring result for human sleep according to the characteristic information. This circuit has a simple structure, can realize the switch between the sleep monitoring function and the charging function, and is low-cost. Moreover, the introduction of electrode patch makes the monitoring apparatus more portable and waterproof, improves the service life, and at the same time avoids occurrence of an electric leakage accident and an electric shock accident.

Figure 2:
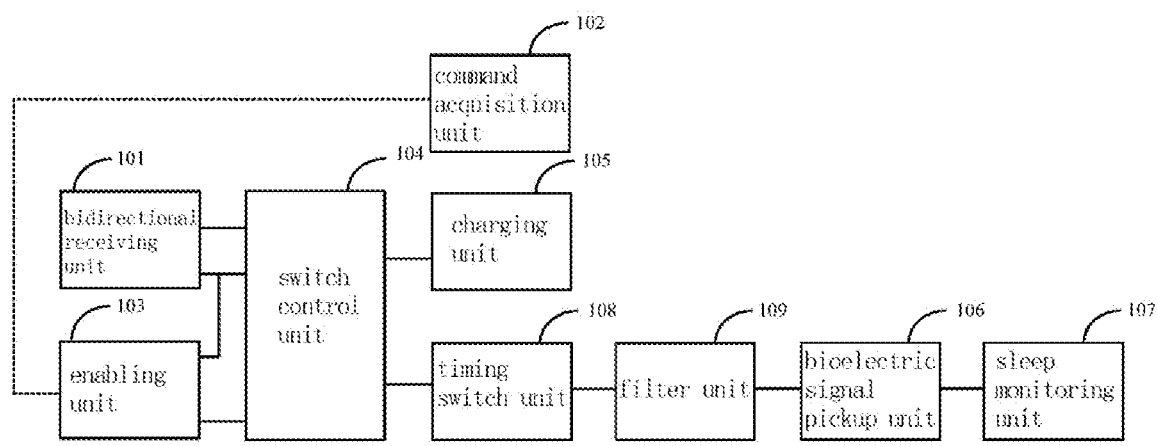
FIG. 2 is another structural schematic diagram of the sleep monitoring circuit according to an embodiment of the present application.

On the basis of the architecture as shown in FIG. 1, FIG. 2 shows another unit structure of the sleep monitoring control circuit according to an embodiment of the present application. For convenience of illustration, only the parts related to the embodiments of the present application are shown, which are detailed as follows.

The sleep monitoring circuit includes a bidirectional receiving unit 101, a command acquisition unit 102, an enabling unit 103, a switch control unit 104, a charging unit 105, a bioelectric signal pickup unit 106, a sleep monitoring unit 107, a timing switch unit 108, and a filter unit 109.

In an embodiment of the present application, the first output end of the bidirectional receiving unit 101 is connected with the input end of the switch control unit 104, the enabling end of the enabling unit 103 is connected with the output end of the command acquisition unit 102, the second output end of the bidirectional receiving unit 101, the input end of the enabling unit 103 and the first enabling end of the switch control unit 104 are connected together, the output end of the enabling unit 103 is connected with the second enabling end of the switch control unit 104, the first output end of the switch control unit 104 is connected with the input end of the charging unit 105, the second output end of the switch control unit 104 is connected with an input end of the timing switch unit 108, an output end of the timing switch unit 108 is connected with an input end of the filter unit 109, an output end of the filter unit 109 is connected with the input end of the bioelectric signal pickup unit 106, and the output end of the bioelectric signal pickup unit 106 is connected with the sleep monitoring unit 107.

In an embodiment of the present application, related descriptions for the bidirectional receiving unit 101, the command acquisition unit 102, the enabling unit 103, the switch control unit 104, the charging unit 105, the bioelectric signal pickup unit 106, and the sleep monitoring unit 107 are as above, which will be not repeated herein again in order to save space.

In an embodiment of the present application, the timing switch unit 108 is configured to be turned on regularly and access the bioelectrical signal, and output the accessed bioelectric signal to the filter unit 109. The input end of the timing switch unit 108 is connected with the second output end of the switch control unit 104, and the output end of the timing switch unit 108 is connected with the input end of the filter unit 109. It should be noted that, the timing switch unit 108 is configured to be turned on regularly and access the bioelectric signal so as to indirectly promote the sleep monitoring unit 107 to monitor human sleep regularly, thereby saving electric energy and improving monitoring efficiency. Therefore, a circuit is qualified as long as the circuit is capable of realizing the function of the timing switch unit 108, and the timing time is set according to the user's need.

In an embodiment of the present application, the filter unit 109 is configured to filter the bioelectric signal and output the filtered bioelectric signal to the bioelectric signal pickup unit 106. Among them, the filtering refers to filtering defects in the bioelectric signal to improve the accuracy and reliability of the subsequent monitoring result. Specifically, the filter unit 109 may be composed of a plurality of resistors and filter capacitor elements.

In the sleep monitoring circuit provided in this embodiment of the present application, when the electrode patch accesses the power signal, the switch control unit 104 generates the charging control signal according to the power signal so as to control the charging unit 105 to implement the charging management; when the electrode patch accesses the bioelectrical signal, the command acquisition unit 102 acquires the sleep monitoring command from the user so as to trigger the enabling unit 103 to generate the monitoring switch signal, the switch control unit 104 outputs the bioelectric signal to the timing switch unit 108 and the filter unit 109 according to the monitoring switch signal, the bioelectric signal pickup unit 106 regularly accesses the bioelectric signal with the defects filtered out and extracts the characteristic information therein and outputs the characteristic information to the sleep monitoring unit 107 through the timing conduction of the timing switch unit 108 and the filtering of the filter unit 109, and the sleep monitoring unit 107 generates the monitoring result for human sleep according to the characteristic information. This circuit has a simple structure, can realize the switch between the sleep monitoring function and the charging function and monitor the sleep for the user regularly, and is low-cost. Moreover, the introduction of electrode patch makes the monitoring apparatus more portable and waterproof, improves the service life, and at the same time avoids occurrence of an electric leakage accident and an electric shock accident.

Figure 3:
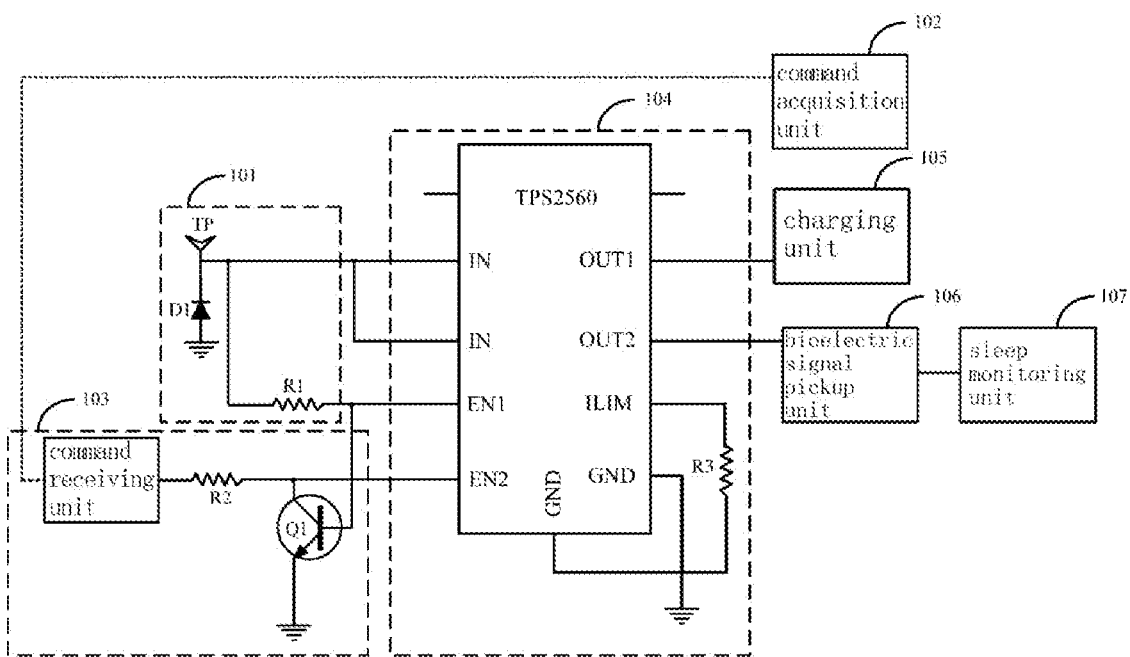
FIG. 3 is an exemplary circuit diagram of the sleep monitoring circuit according to an embodiment of the present application.

FIG. 3 (corresponding to FIG. 1) shows a specific circuit structure of the sleep monitoring control circuit according to an embodiment of the present application. For convenience of illustration, only the parts related to the embodiments of the present application are shown, which are detailed as follows.

As shown in FIG. 3, the bidirectional receiving unit 101 includes an electrode patch TP, a diode D1 and a first resistor R1.

Specifically, an anode of the diode D1 is grounded, a cathode of the diode D1, a first end of the first resistor R1 and the electrode patch TP are connected together to form the first output end of the bidirectional receiving unit 101, and a second end of the first resistor R1 is the second output end of the bidirectional receiving unit 101. The electrode patch TP receives the power signal from the charging apparatus or the bioelectric signal from the human body, outputs the power signal or bioelectric signal directly from the first output end to the input end of the switch control unit 104, and at the same time outputs the power signal or bioelectric signal to the first enabling end of the switch control unit 104 through the first resistor R1.

As shown in FIG. 3, the enabling unit 103 includes a command receiving unit, a second resistor R2 and a first switch tube Q1.

Specifically, an input end of the command receiving unit is the enabling end of the enabling unit 103, an output end of the command receiving unit is connected with a first end of the second resistor R2, a control end of the first switch tube Q1 is the input end of the enabling unit 103, a current output end of the first switch tube Q1 is grounded, and a second end of the second resistor R2 and a current input end of the first switch tube Q1 are connected together to form the output end of the enabling unit 103. Among them, the command receiving unit is configured to receive the sleep monitoring command(i.e., the voltage signal of 2.7V-12V) output by the command acquisition unit 102, and may be specifically a RF receiving circuit including an antenna, and the RF receiving circuit is coupled to receive the sleep monitoring command through the antenna. The first switch tube Q1 may be an NPN-typed triode, and a collector of the NPN-typed triode is the current input end of the first switch tube Q1, an emitter of the NPN-typed triode is the current output end of the first switch tube Q1, and a base of the NPN-typed triode is the control end of the first switch tube Q1.

The NPN-typed triode is taken as an example and the above enabling unit 103 is further explained below by combining the operation principle: the input of the base of the NPN-typed triode comes from the bioelectric signal output by the bidirectional receiving unit 101, and at the same time the command receiving unit receives the voltage signal of 2.7V-12Voutput by the command acquisition unit 102, and outputs the voltage signal to the collector of the NPN-typed triode through the second resistor R2,thereby the NPN-typed triode is turned on and outputs the voltage signal to the switch control unit 104.

As shown in FIG. 3, the switch control unit 104 includes a dual-channel switch control chip U and a third resistor R3.

Two input ends IN of the dual-channel switch control chip U are the input end of the switch control unit 104, a first enabling end EN1 and a second enabling end EN2 of the dual-channel switch control chip U are respectively the first enabling end and the second enabling end of the switch control unit 104, a first output end OUT1 and a second output end OUT2 of the dual-channel switch control chip U are respectively the first output end and the second output end of the switch control unit 104, a current-limiting end ILIM of the dual-channel switch control chip U is connected to a first end of the third resistor R3, and a second end of the third resistor R3 and two grounding ends GND of the dual-channel switch control chip U are grounded together.

Among them, the dual-channel switch control chip U may specifically select a chip with model being TPS2560.

The switch control unit 104 described above is further explained below in combination with the operation principles: when the input end IN and the first enabling end EN1 of the dual-channel switch control chip U access the power signal, the first switch channel of the dual-channel switch control chip U is turned on, the dual-channel switch control chip U generates the charging control signal and outputs the charging control signal from the first output end OUT1 to the charging unit 105; when the input end IN of the dual-channel switch control chip U accesses the bioelectric signal and the second enabling end EN2 accesses the monitoring switch signal, the second switch channel of the dual-channel switch control chip U is turned on, and the dual-channel switch control chip U outputs the input bioelectric signal from the second output end OUT2 to the bioelectric signal pickup unit 106. Among them, the third resistor R3 is connected to the current-limiting end ILIM of the dual-channel switch control chip U for current-limiting protection for the chip.

Therefore, in the sleep monitoring circuit provided in the embodiments of the present application, when the electrode patch TP accesses the power signal, the switch control unit 104 generates the charging control signal according to the power signal so as to control the charging unit 105 to perform the charging management; when the electrode patch TP accesses the bioelectrical signal, the command acquisition unit 102 acquires the sleep monitoring command from the user so as to trigger the enabling unit 103 to generate the monitoring switch signal, the switch control unit 104 outputs the bioelectric signal to the bioelectric signal pickup unit 106 according to the monitoring switch signal, the bioelectric signal pickup unit 106 extracts the characteristic information from the bioelectric signal and outputs the characteristic information to the sleep monitoring unit 107, and the sleep monitoring unit 107 generates the monitoring result for human sleep according to the characteristic information. This circuit has a simple structure, can realize the switch between the sleep monitoring function and the charging function, and is low-cost. Moreover, the introduction of electrode patch TP makes the monitoring apparatus more portable and waterproof, improves the service life, and at the same time avoids occurrence of an electric leakage accident and an electric shock accident.

An embodiment of the present application provides a sleep monitoring apparatus, which includes the sleep monitoring circuit described as above, wherein the electrode patch is plugged into the base of the charging apparatus or fit on the skin surface of the human body. When the electrode patch accesses the power signal, the sleep monitoring apparatus may implement charging management; when the electrode patch accesses the bioelectrical signal, the sleep monitoring apparatus may monitor the human sleep according to the monitoring result of the human sleep. The sleep monitoring apparatus is provided with a waterproof function and long service life, and is easy to be worn and used by the user, being capable of improving the user experience.

In this specification, a specific example is applied to explain the principle and implementations of the present application, and the description for the above embodiments is only used to help understand the method and key idea of the present application. It should be pointed out that, several improvements and modifications may be made to the present application for a person of ordinary skill in the art without departing from the principle of the present application, and these improvements and modifications also fall within the protection scope of the claims of the present application.

The above description only describes preferable embodiments of the present application and is not intended to limit the present application. Any modification, equivalent substitution and improvement made within the spirit and principle of the present application shall be included in the protection scope of the present application.

What is claimed is:

1. A sleep monitoring circuit, comprising:
   a bidirectional receiving unit comprising an electrode patch, wherein the electrode patch receives a power signal from a charging apparatus when in connection with the charging apparatus, and receives a bioelectric signal from a human body when in connection with the human body;
   a command acquisition unit configured to acquire a sleep monitoring command from a user;
   an enabling unit configured to generate a monitoring switch signal according to the bioelectric signal and the sleep monitoring command, wherein an input end of the enabling unit is connected with the bidirectional receiving unit, and an enabling end of the enabling unit is connected with an output end of the command acquisition unit;
   a switch control unit configured to switch between a sleep monitoring function and a charging function, to generate a charging control signal according to the power signal, and to output the bioelectric signal according to the monitoring switch signal, wherein an input end of the switch control unit is connected with a first output end of the bidirectional receiving unit, and wherein a first enabling end of the switch control unit, a second output end of the bidirectional receiving unit and the input end of the enabling unit are in common connection, and a second enabling end of the switch control unit is connected with an output end of the enabling unit;
   a charging circuit configured to implement charging management according to the charging control signal, wherein an input end of the charging circuit is connected with a first output end of the switch control unit;
   a bioelectric signal pickup unit configured to perform extraction on the bioelectric signal output by the switch control unit for generating characteristic information of the bioelectric signal, wherein an input end of the bioelectric signal pickup unit is connected with a second output end of the switch control unit;
   a sleep monitoring unit configured to monitor and analyze the characteristic information and to generate a monitoring result for human sleep, wherein an input end of the sleep monitoring unit is connected with an output end of the bioelectric signal pickup unit.

2. The sleep monitoring circuit according to claim 1, wherein the sleep monitoring circuit further comprises:
   a filter unit configured to filter the bioelectric signal and output the filtered bioelectric signal to the bioelectric signal pickup unit, wherein an input end of the filter unit is connected with the second output end of switch control unit, and an output end of the filter unit is connected with the input end of the bioelectric signal pickup unit.

3. The sleep monitoring circuit according to claim 2, wherein the sleep monitoring circuit further comprises:
   a timing switch unit configured to be turned on regularly and output the accessed bioelectric signal to the filter unit, wherein an input end of the timing switch unit is connected with the second output end of the switch control unit, and an output end of the timing switch unit is connected with the input end of the filter unit.

4. The sleep monitoring circuit according to claim 1, wherein the bidirectional receiving unit comprises:
the electrode patch, a diode D1, and a first resistor R1;
wherein an anode of the diode D1 is grounded, a cathode of the diode D1, a first end of the first resistor R1 and the electrode patch are connected together to form the first output end of the bidirectional receiving unit, and a second end of the first resistor R1 is the second output end of the bidirectional receiving unit.

5. The sleep monitoring circuit according to claim 1, wherein the enabling unit comprises:
a command receiving unit, a second resistor R2, and a first switch tube;
wherein an input end of the command receiving unit is the enabling end of the enabling unit, an output end of the command receiving unit is connected with a first end of the second resistor R2, a control end of the first switch tube is the input end of the enabling unit, a current output end of the first switch tube is grounded, and a second end of the second resistor R2 and a current input end of the first switch tube are connected together to form the output end of the enabling unit.

6. The sleep monitoring circuit according to claim 5, wherein the first switch tube is an NPN-typed triode, a collector of the NPN-typed triode is the current input end of the first switch tube, an emitter of the NPN-typed triode is the current output end of the first switch tube, and a base of the NPN-typed triode is the control end of the first switch tube.

7. The sleep monitoring circuit according to claim 1, wherein the switch control unit comprises:
a dual-channel switch control chip and a third resistor R3;
wherein two input ends of the dual-channel switch control chip are the input ends of the switch control unit, a first enabling end and a second enabling end of the dual-channel switch control chip are respectively the first enabling end and the second enabling end of the switch control unit, a first output end and a second output end of the dual-channel switch control chip are respectively the first output end and the second output end of the switch control unit, a current-limiting end of the dual-channel switch control chip is connected to a first end of the third resistor, and a second end of the third resistor and two grounding ends of the dual-channel switch control chip are grounded together.

8. The sleep monitoring circuit according to claim 1, wherein the power signal ranges from 4.5V to 5.2V, and a voltage of the bioelectric signal is not greater than 0.1V.

9. The sleep monitoring circuit according to claim 1, wherein a voltage of the monitoring switch signal ranges from 2.7V to 12V.

10. A sleep monitoring apparatus, comprising:
a sleep monitoring circuit, comprising:
a bidirectional receiving unit comprising an electrode patch, wherein the electrode patch receives a power signal from a charging apparatus when in connection with the charging apparatus, and receives a bioelectric signal from a human body when in connection with the human body;
a command acquisition unit configured to acquire a sleep monitoring command from a user;
an enabling unit configured to generate a monitoring switch signal according to the bioelectric signal and the sleep monitoring command, wherein an input end of the enabling unit is connected with the bidirectional receiving unit, and an enabling end of the enabling unit is connected with an output end of the command acquisition unit;
a switch control unit configured to switch between a sleep monitoring function and a charging function, to generate a charging control signal according to the power signal, and to output the bioelectric signal according to the monitoring switch signal, wherein an input end of the switch control unit is connected with a first output end of the bidirectional receiving unit, and wherein a first enabling end of the switch control unit, a second output end of the bidirectional receiving unit and the input end of the enabling unit are in common connection, and a second enabling end of the switch control unit is connected with an output end of the enabling unit;
a charging circuit configured to implement charging management according to the charging control signal, wherein an input end of the charging circuit is connected with a first output end of the switch control unit;
a bioelectric signal pickup unit configured to perform extraction on the bioelectric signal output by the switch control unit for generating characteristic information of the bioelectric signal, wherein an input end of the bioelectric signal pickup unit is connected with a second output end of the switch control unit;
a sleep monitoring unit configured to monitor and analyze the characteristic information and to generate a monitoring result for human sleep, wherein an input end of the sleep monitoring unit is connected with an output end of the bioelectric signal pickup unit,
wherein the electrode patch is plugged into a base of the charging apparatus or fit on a skin surface of a human body.

11. The sleep monitoring apparatus according to claim 10, wherein the sleep monitoring circuit further comprises:
a filter unit configured to filter the bioelectric signal and output the filtered bioelectric signal to the bioelectric signal pickup unit, wherein an input end of the filter unit is connected with the second output end of switch control unit, and an output end of the filter unit is connected with the input end of the bioelectric signal pickup unit.

12. The sleep monitoring apparatus according to claim 11, wherein the sleep monitoring circuit further comprises:
a timing switch unit configured to be turned on regularly and output the accessed bioelectric signal to the filter unit, wherein an input end of the timing switch unit is connected with the second output end of the switch control unit, and an output end of the timing switch unit is connected with the input end of the filter unit.

13. The sleep monitoring apparatus according to claim 10, wherein the bidirectional receiving unit comprises:
the electrode patch, a diode D1, and a first resistor R1;
wherein an anode of the diode D1 is grounded, a cathode of the diode D1, a first end of the first resistor R1 and the electrode patch are connected together to form the first output end of the bidirectional receiving unit, and a second end of the first resistor R1 is the second output end of the bidirectional receiving unit.

14. The sleep monitoring apparatus according to claim 10, wherein the enabling unit comprises:

a command receiving unit, a second resistor R2, and a first switch tube;

wherein an input end of the command receiving unit is the enabling end of the enabling unit, an output end of the command receiving unit is connected with a first end of the second resistor R2, a control end of the first switch tube is the input end of the enabling unit, a current output end of the first switch tube is grounded, and a second end of the second resistor R2 and a current input end of the first switch tube are connected together to form the output end of the enabling unit.

15. The sleep monitoring apparatus according to claim 14, wherein the first switch tube is an NPN-typed triode, a collector of the NPN-typed triode is the current input end of the first switch tube, an emitter of the NPN-typed triode is the current output end of the first switch tube, and a base of the NPN-typed triode is the control end of the first switch tube.

16. The sleep monitoring apparatus according to claim 10, wherein the switch control unit comprises:

a dual-channel switch control chip and a third resistor R3;

wherein two input ends of the dual-channel switch control chip are the input ends of the switch control unit, a first enabling end and a second enabling end of the dual-channel switch control chip are respectively the first enabling end and the second enabling end of the switch control unit, a first output end and a second output end of the dual-channel switch control chip are respectively the first output end and the second output end of the switch control unit, a current-limiting end of the dual-channel switch control chip is connected to a first end of the third resistor, and a second end of the third resistor and two grounding ends of the dual-channel switch control chip are grounded together.

17. The sleep monitoring apparatus according to claim 10, wherein the power signal ranges from 4.5V to 5.2V, and a voltage of the bioelectric signal is not greater than 0.1V.

18. The sleep monitoring apparatus according to claim 10, wherein a voltage of the monitoring switch signal ranges from 2.7V to 12V.

* * * * *